US006811222B1

(12) United States Patent
Sumner

(10) Patent No.: US 6,811,222 B1
(45) Date of Patent: Nov. 2, 2004

(54) CHIN AND NECK BRACE

(76) Inventor: Cynthia K. Sumner, P.O. Box 524, Lexington, OR (US) 97839

( * ) Notice: Subject to any disclaimer, the term of this patent is extended or adjusted under 35 U.S.C. 154(b) by 0 days.

(21) Appl. No.: 10/458,146

(22) Filed: Jun. 9, 2003

Related U.S. Application Data

(60) Provisional application No. 60/387,224, filed on Jun. 10, 2002.

(51) Int. Cl.[7] .......................... A47C 7/38; A47D 15/00; A62B 35/00
(52) U.S. Cl. .................. 297/392; 297/393; 297/397; 297/465; 297/484; 297/485; 297/487; 297/488
(58) Field of Search .............................. 297/392, 393, 297/397, 465, 484, 485, 487, 488

(56) References Cited

U.S. PATENT DOCUMENTS

| | | | | |
|---|---|---|---|---|
| 2,774,601 A | * | 12/1956 | White ..................... 297/392 X |
| 2,851,033 A | * | 9/1958 | Thornton ................ 297/484 X |
| 3,008,464 A | * | 11/1961 | Atkins ..................... 297/393 X |
| 3,320,950 A | * | 5/1967 | McElvenny ............. 297/393 X |
| 3,466,090 A | * | 9/1969 | Posey ......................... 297/484 |
| 3,536,357 A | * | 10/1970 | Murcott ..................... 297/485 |
| 3,565,483 A | * | 2/1971 | Posey ......................... 297/484 |
| 3,604,750 A | * | 9/1971 | Doering ...................... 297/467 |
| 4,026,448 A | * | 5/1977 | Lewis .................... 297/392 X |
| 4,050,737 A | * | 9/1977 | Jordan ................... 297/485 X |
| 4,170,991 A | * | 10/1979 | Kella ......................... 297/467 |
| 4,345,347 A | | 8/1982 | Kantor .......................... 5/441 |
| 4,401,111 A | | 8/1983 | Blackstone ................... 128/75 |
| 4,565,408 A | * | 1/1986 | Palley ......................... 297/393 |
| 4,712,540 A | | 12/1987 | Tucker et al. ................ 128/76 |
| 4,807,937 A | * | 2/1989 | Harrigan ..................... 297/465 |
| 4,848,793 A | * | 7/1989 | Huspen ................... 297/465 X |
| 4,886,315 A | * | 12/1989 | Johnson ................. 297/484 X |
| 4,979,779 A | * | 12/1990 | Williams ..................... 297/465 |
| 5,020,174 A | | 6/1991 | Sarkozi ......................... 5/437 |
| 5,108,152 A | * | 4/1992 | Reilly et al. ........... 297/484 X |
| 5,123,132 A | | 6/1992 | Dixon ........................... 5/636 |
| 5,154,487 A | * | 10/1992 | Warburton .................. 297/465 |
| 5,297,852 A | * | 3/1994 | Morales-Quintero .... 297/485 X |
| 5,730,498 A | * | 3/1998 | Hanson et al. .............. 297/465 |
| 6,000,401 A | | 12/1999 | Herrick ....................... 128/869 |
| 6,042,189 A | * | 3/2000 | Wellman ..................... 297/465 |
| 6,219,865 B1 | * | 4/2001 | Stokesbary ............. 297/392 X |
| 6,230,712 B1 | | 5/2001 | Kohnke ....................... 128/869 |
| 6,247,756 B1 | * | 6/2001 | Wagner ....................... 297/484 |
| 6,408,467 B2 | | 6/2002 | Walpin ........................ 5/636 |
| 6,513,176 B1 | | 2/2003 | Najar ............................. 4/523 |
| 6,513,824 B2 | * | 2/2003 | DuBose ................. 297/465 X |
| 6,523,200 B2 | | 2/2003 | Brown .......................... 5/639 |
| 6,536,058 B1 | | 3/2003 | Chang .......................... 5/636 |
| 2003/0038520 A1 | * | 2/2003 | Marbutt ...................... 297/392 |
| 2004/0026979 A1 | * | 2/2004 | Haddon ...................... 297/393 |

* cited by examiner

*Primary Examiner*—Rodney B. White
(74) *Attorney, Agent, or Firm*—Floyd E. Ivey; Liebler, Ivey, Connor, Berry & St. Hilaire

(57) ABSTRACT

This invention discloses a chin and head support device or brace enabling the head to move at will while allowing a rest at the chin and while supporting the weight of the head.

10 Claims, 11 Drawing Sheets

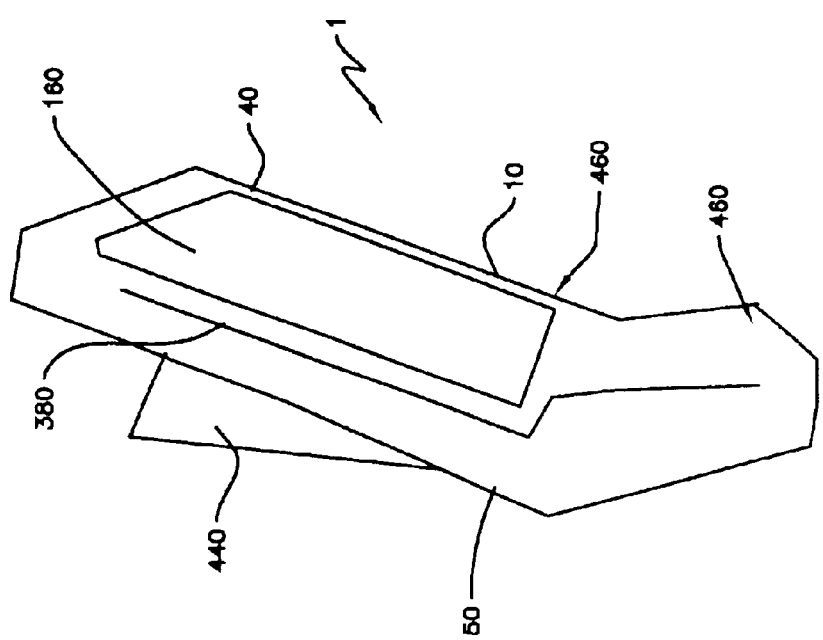

CHIN AND NECK BRACE

PROVISIONAL APPLICATION

This application is pending from Provisional Application 60/387,224, filed Jun. 10, 2002.

FIELD OF THE INVENTION

This invention relates to a chin and head support device and more particularly a chin and head support or brace enabling the head to move at will while allowing a rest at the chin and while supporting the weight of the head.

BACKGROUND OF THE INVENTION

Other devices, including cervical collars and head supports, are seen in the art which supports the head and neck including U.S. Pat. No. 4,345,347 to Kantor; U.S. Pat. No. 6,000,401 to Herrick; U.S. Pat. No. 5,020,174 to Sarkozi; U.S. Pat. No. 6,408,467 to Walpin; U.S. Pat. No. 6,536,058 to Chang; U.S. Pat. No. 6,523,200 to Brown; U.S. Pat. No. 4,401,111 to Blackstone; U.S. Pat. No. 4,712,540 to Tucker, et al; U.S. Pat. No. 6,513,176 to Najar; U.S. Pat. No. 5,123,132 to Dixon and U.S. Pat. No. 6,230,712 to Koslashed.hnke. The patents referred to herein are provided herewith in an Informnation Disclosure Statement in accordance with 37 CFR 1.97.

SUMMARY OF THE INVENTION

Particular medical conditions limit patients to wheelchair mobility and support where the patient has limited cervical or neck muscle and head control. This invention provides a brace and support for the neck and head for the wheelchair bound patient. This invention discloses a brace assembly that supports the chin while not binding the neck or hear or restraining head and neck movement.

The shape of the brace where contacted by a patient's chin and neck is formed to provide comfort to the chin and neck with this facilitated by the shape of the brace and of the interior foam. For use with patients, the brace assembly is small and is formed of materials which are easy to clean while offering the patient a smooth surface thus leaving the patient's head mobile. The patient's chin rests on the brace in the front to hold the weight of the patient's head. The brace assembly includes affixing means including, in the preferred embodiment, velcro straps on both sides that attach to shoulder bars on a wheelchair or at other locations depending on the circumstance of the patient. An alternative embodiment, for the wheelchair bound patient, is not affixed to shoulder bars but rather to an assembly which is secured to the patient's body presenting the brace assembly to the patient in much the same orientation as if it were affixed to a wheelchair.

The bottom edge of the brace has a opening and closing means, including a zipper, where an interior form, generally composed of foam, is inserted and removed. In the preferred embodiment a Velcro® backed slip cover is received over the top edge of the brace and can be changed as needed. This brace has a distinct front and back, with the upfacing "c" shape of the top edge supporting the chin thus making television, eye examinations and other viewing more easily accomplished. The brace assists the patient in alignment of the patient's spine and positioning in a wheelchair or other circumstance thus reducing patient fatigue.

BRIEF DESCRIPTION OF THE DRAWINGS

The foregoing and other features and advantages of the present invention will become more readily appreciated as the same become better understood by reference to the following detailed description of the preferred embodiment of the invention when taken in conjunction with the accompanying drawings, wherein:

FIG. 11 is a section from FIG. 8 showing the brace with a brace positioning means.

DETAILED DESCRIPTION

Figure 1:
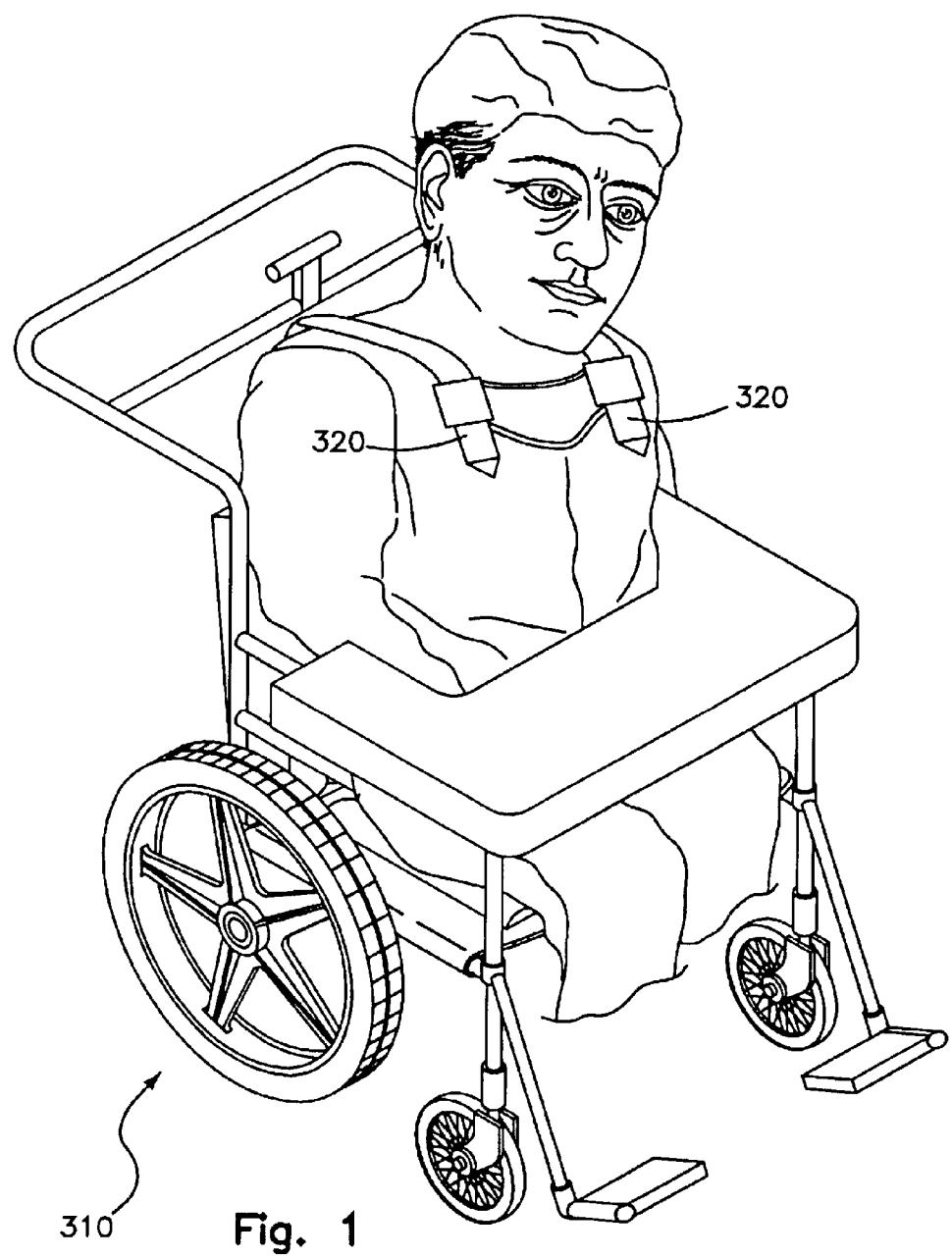
FIG. 1 is a perspective view of a patient in a wheelchair showing shoulder bars without representation of the invention.

The immediate use of the disclosed invention is to provide head and neck support to a wheelchair bound patient. A wheelchair bound patient is shown in FIG. 1 without demonstration of use of the invention. FIG. 1 illustrates a wheelchair (310) with shoulder bars (320) which offer support and restraint for a patient.

The invention is depicted in FIG. 2-6 showing a brace assembly (1) comprising substantially planar brace (10) having a top edge (20), a bottom edge (30), a front side (40) and a back side (50), and a first side (60) and a second side (70). The top edge (20) forms an upfacing "c" or "u" shape which receives and supports a patient's chin. The brace (10) having a width "w1" (90), from the front side (40) to the back side (50), intermediate the top edge (20) and the bottom edge and the top edge (20) having a width "w2" (100) from the front side (40) to the back side (50) so that the width of "w2" (100) is less than the width "w1" (90); this difference in width "w1" (90) and width "w2" (100) creates a sloping portion between the top edge (20) and the brace (10) proximal the top edge (20) which is accommodating of a patient's chin, i.e., the shape provided at the top edge (20) and at the front side (40) proximal the top edge (20) allows the patient's chin and neck to receive support while reducing any the structure which would obstruct the chin and neck while the head turns.

It is seen that the brace assembly (1) is secured to the wheelchair (310) at the shoulder bars (320). It will be appreciated by those of ordinary skill in the arts that the invention may be used for patient support in circumstances other than when the patient is in a wheel chair. The means of securing the brace assembly (1) is provided by a first shoulder bar attaching means (110) affixed by affixing means to the first side (60) and extending from the first side (60); a second shoulder bar attaching means (120) affixed by affixing means to the second side (70) and extending from the second side (70). Affixing means to attach the first shoulder bar attaching means (110) and the second shoulder bar attaching means (120) respectively to the first side (60) and the second side (70) provided by but not limited to sewing, adhesives, snaps and other affixing means as will be appreciated by those of ordinary skills in the sewing and pillow and related arts.

It will be seen in FIG. 2 through 6 that the brace assembly (1), in the preferred embodiment, is generally formed of a planar brace (10) having an outside (130) and an inside (140); opening and closing means (150) at one or more of the top edge (20), bottom edge, first side (60), second side (70), front side (40) and back side (50); the opening and closing means (150) comprised of an opening at one or more of said locations on the brace assembly (1) which, when opened allows insertion or retraction of an interior form (160) to the inside (140); the opening and closing means (150) when closed retaining the interior form (160) at the inside (140). The opening and closing means (150) will be appreciated to be additionally comprised of an form receiving opening (150) from the outside (130) to the inside (140) with the form receiving opening (150) secured by opening and closing means including zipper, Velcro®; snaps or other devices allowing the securing of an opening.

Of particular interest in the preferred embodiment is the structure of the brace assembly (1) at and proximal the top edge (20). It will be appreciated from FIG. 4 that the width of the brace (10) increases at the front side (40) from the top edge (20) toward "w1" (90) intermediate the top edge (20) and the bottom edge (30) such that a sloped surface is formed at the front side (40) from the top edge (20) toward "w1" (90) intermediate the top edge (20) and the bottom; it will be seen that the width of the brace assembly (1) increases from width "w1"(90) to width "w2"(100). It is this decreasing width of the brace assembly (1) proximal the top edge (20) which reduces impediments in the movement of the chin and neck as the patient's head turns.

Figure 2:
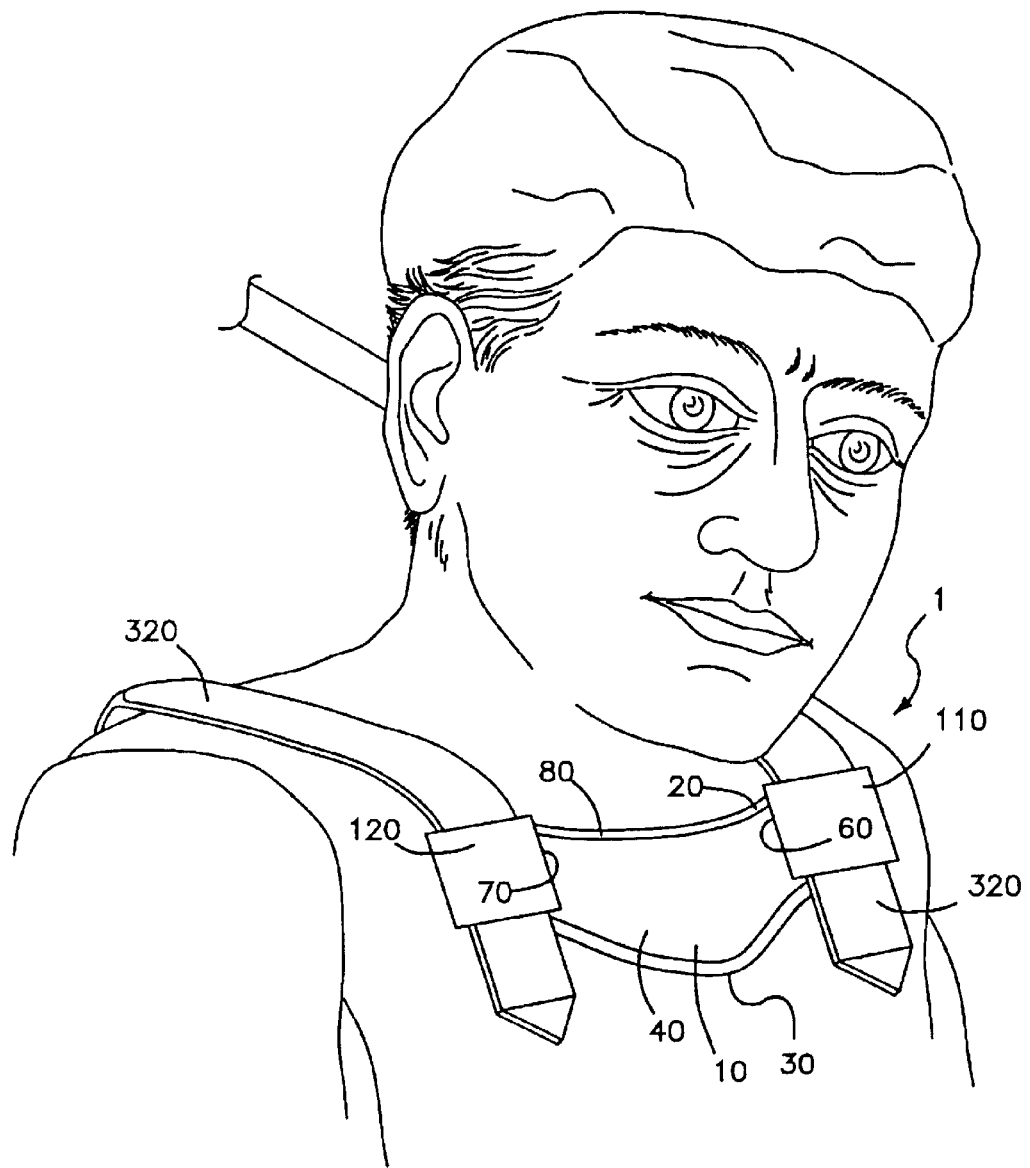
FIG. 2 illustrates the invention affixed to shoulder bars on a wheelchair.
Figure 3:
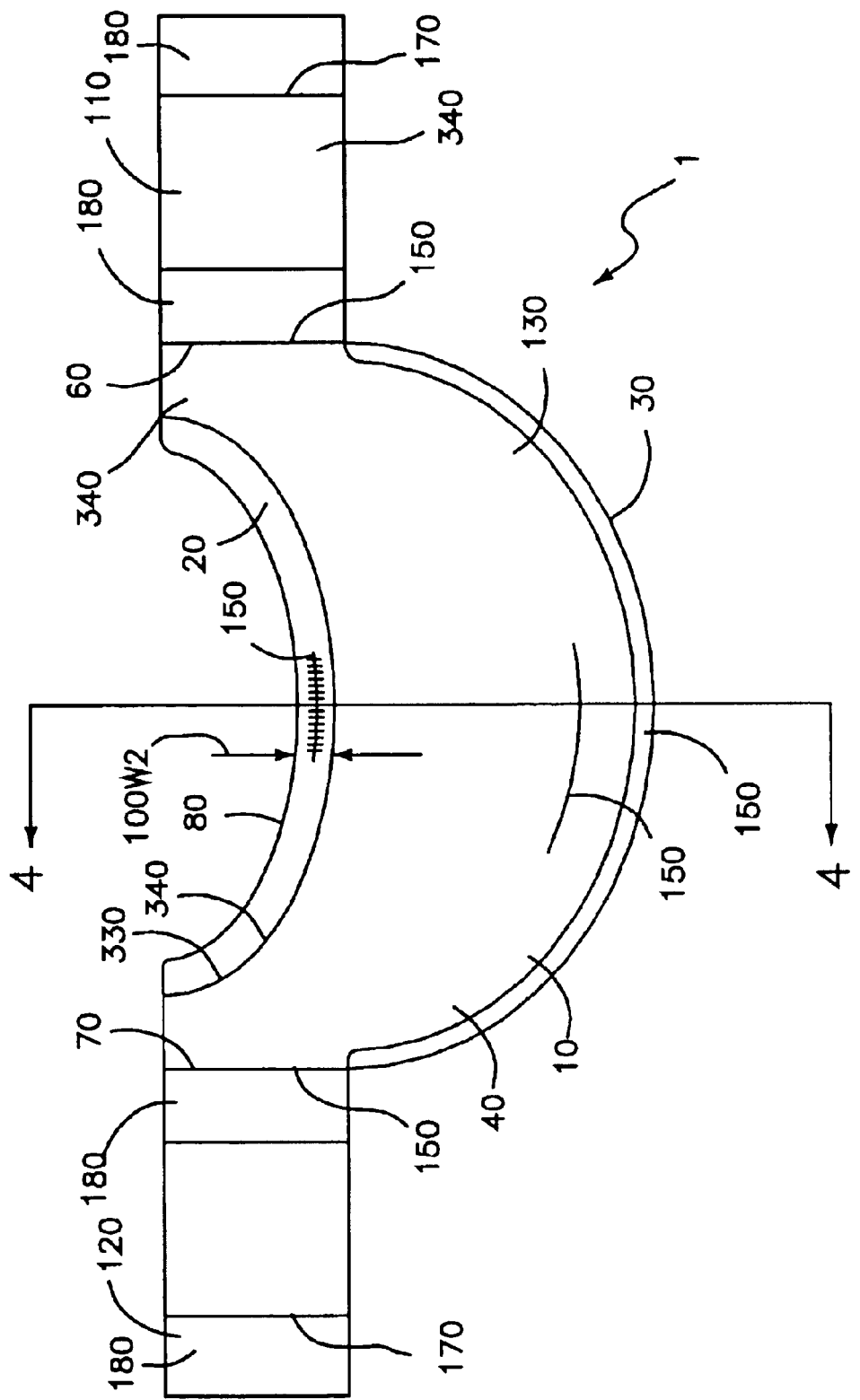
FIG. 3 illustrates a front elevation the brace assembly showing all elements other than the back side.
Figure 4:
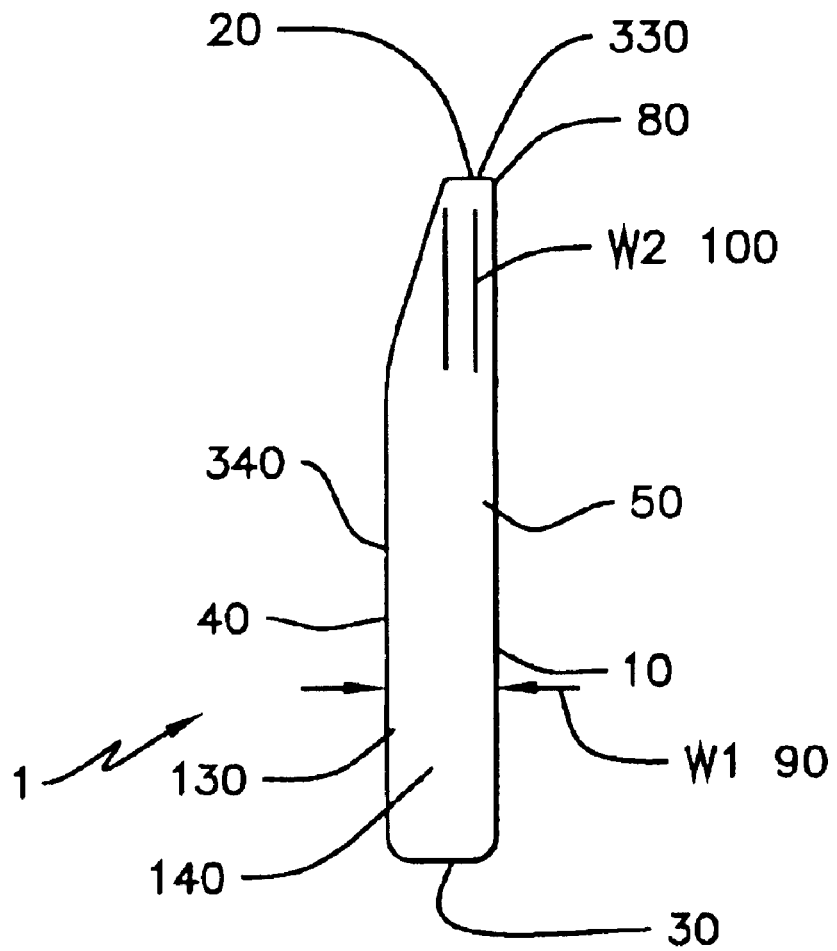
FIG. 4 is a section from FIG. 3 illustrating the diminishing width of the preferred embodiment from width "w1" to width "w2" at the top edge.
Figure 5:
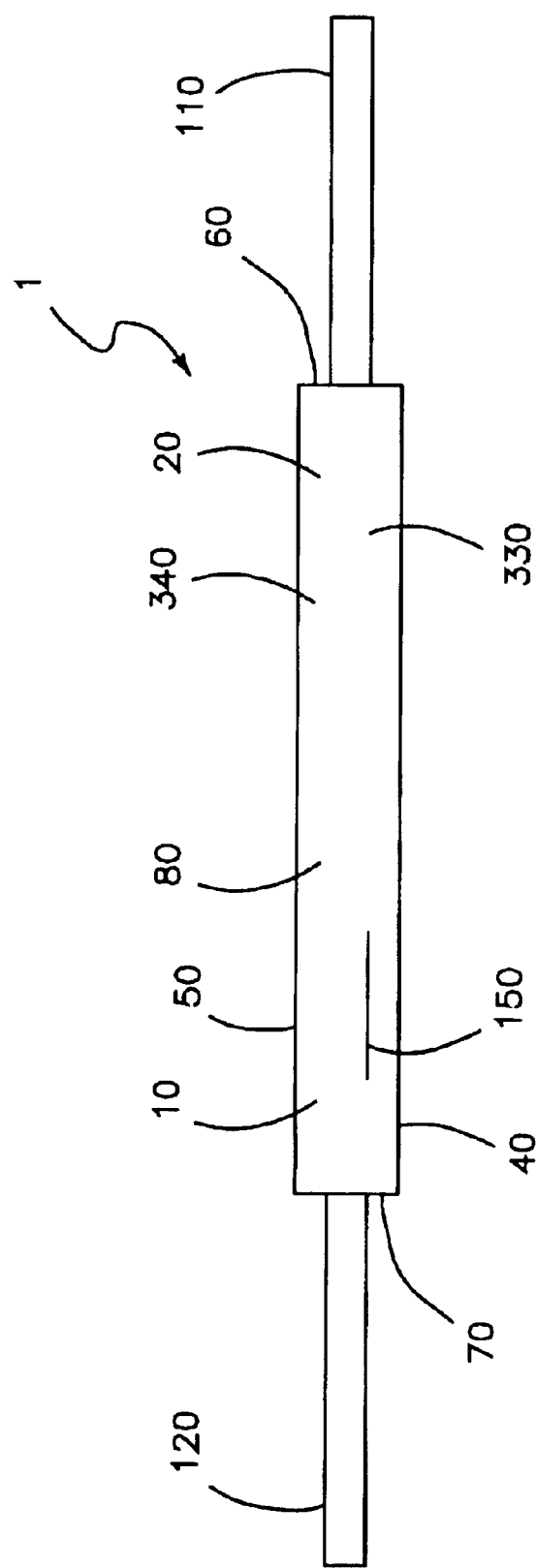
FIG. 5 is a top plan view of the invention.
Figure 6:
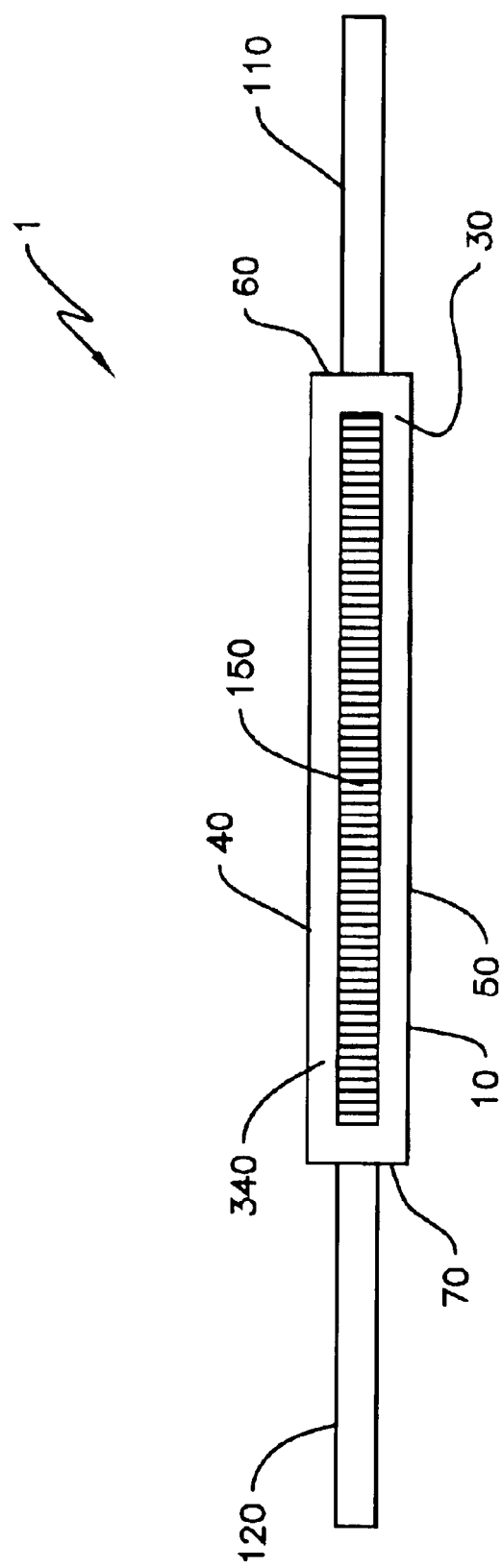
FIG. 6 is a bottom plan view of the invention.

Also seen in FIGS. 2 and 3 is the upfacing "c" shape (80) at the top edge (20) which, in the preferred embodiment, is sized to receive and support a patient's chin. the top edge (20) constructed of a chin and head movement enabling means material (330). It will be appreciated by those of ordinary skills in the sewing and pillow and related arts that movement enabling means material (330) may be comprised of a plastic, Naugahyde, leather, water proofed fabric and other materials which allow ease of movement of the skin of the chin and neck as the chin and neck contact the movement enabling means material (330) during movement of the head. It will also be appreciated that, in the preferred embodiment for use with wheelchair bound patients, that the brace (10) will preferably be formed at one or more of the top edge (20), bottom edge (30), first side (60), second side (70), front side (40) and back side (50) and first shoulder bar attaching means (110) and second shoulder bar attaching means (120) will be constructed from a liquid resistant means material (340) which, as will be appreciated by those of ordinary skills in the sewing arts, may be comprised of a variety of plastic or plastic coated materials and water resistant materials.

In the preferred embodiment the first shoulder bar attaching means (110) and the second shoulder bar attaching means (120) has an affixing surface (170) which comprises or receives an affixing means (180). In the preferred embodiment the affixing means (180) at the affixing surface (170) may be comprised of zippers, Velcro®; snaps or other such affixing devices, e.g., for the preferred embodiment and for simplicity such affixing means allows the first shoulder bar attaching means (110) and the second shoulder bar attaching means (120) to be wrapped around the respective shoulder bars (320) to allow contact of the affixing means (180) thereby securing the brace (10) to the shoulder bars (320) on a wheelchair (310) or to another like structure not limited to either wheelchairs (310) or shoulder bars (320). The first shoulder bar attaching means (110) and the second shoulder bar attaching means (120) are, in the preferred embodiment, comprised of a flexible planar material such as cloth or other pliable fabrics. Those of ordinary skills in the sewing arts will appreciate the range of materials which will suffice including plastics, soil, stain and moisture resistant materials which are generally flexible enough to allow the first shoulder bar attaching means (110) and the second shoulder bar attaching means (120) to be wrapped around a structure, including tubular structures, and to effect attachment.

Figure 7:
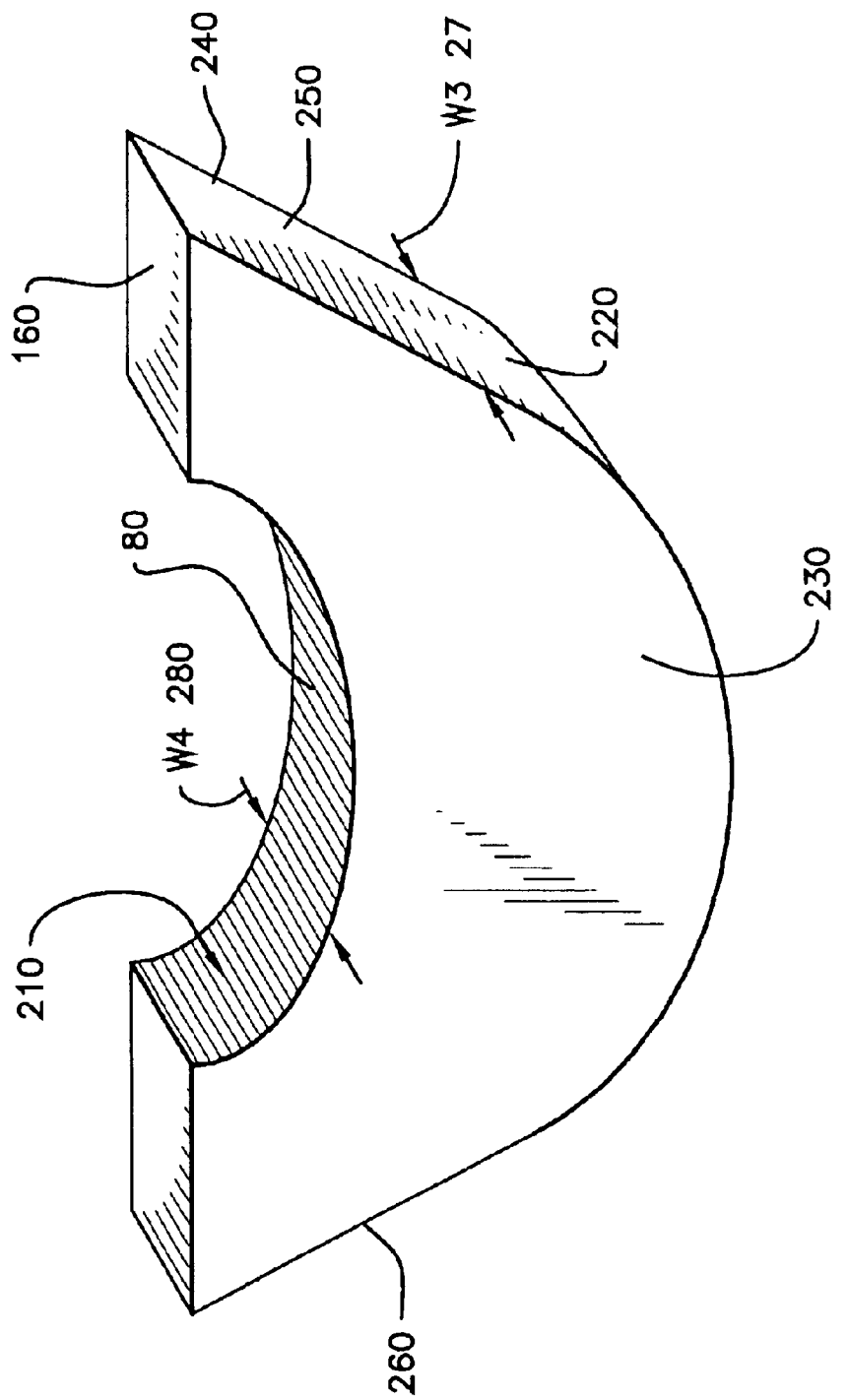
FIG. 7 is a view of the interior formn.

In the preferred embodiment the brace (10) is fitted with an interior form (160), as depicted in FIG. 7, generally having the shape of the brace (10). In the preferred embodiment the interior form (160) is comprised of a semi-rigid material means including a range of firmness of foams including but not limited to foam rubber or polymer foam. However, the structure of the brace (10) itself may conform an interior form (160) to the shape of the brace (10). In the preferred embodiment the interior form (160) has a form top edge (210), a form bottom edge (220), a form front side (230) and a form back side, and a form first side (250) and a form second side (260). In the preferred embodiment the form top edge (210) forms an upfacing "c" shape (80) with the interior form (160) having a width "w3"(270), from the form front side (230) to the form back side (240), intermediate the form top edge (210) and the form bottom edge (220); the form top edge (210) having a width "w4" (280) from the form front side (230) to the form back side (240). In the preferred embodiment the width "w3" (270) is greater than the width "w4"(280). It will be appreciated that in the embodiments where the brace (10) causes the interior form (160) to conform to the shape of the brace (10) that the indicated width "w3" (270) is not required to differ from the width "w4" (280).

Figure 8:
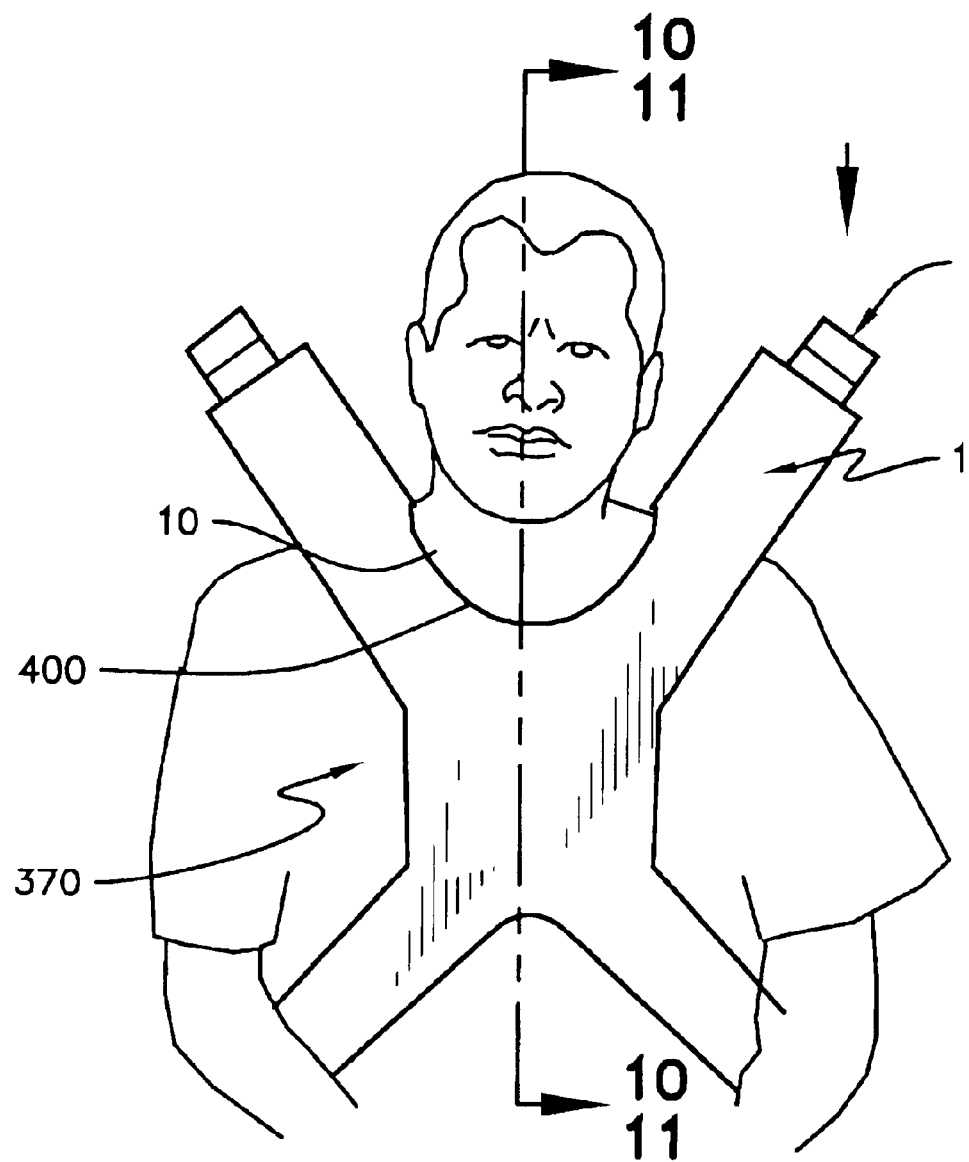
FIG. 8 is a front elevation showing a body harness with brace assembly.
Figure 9:
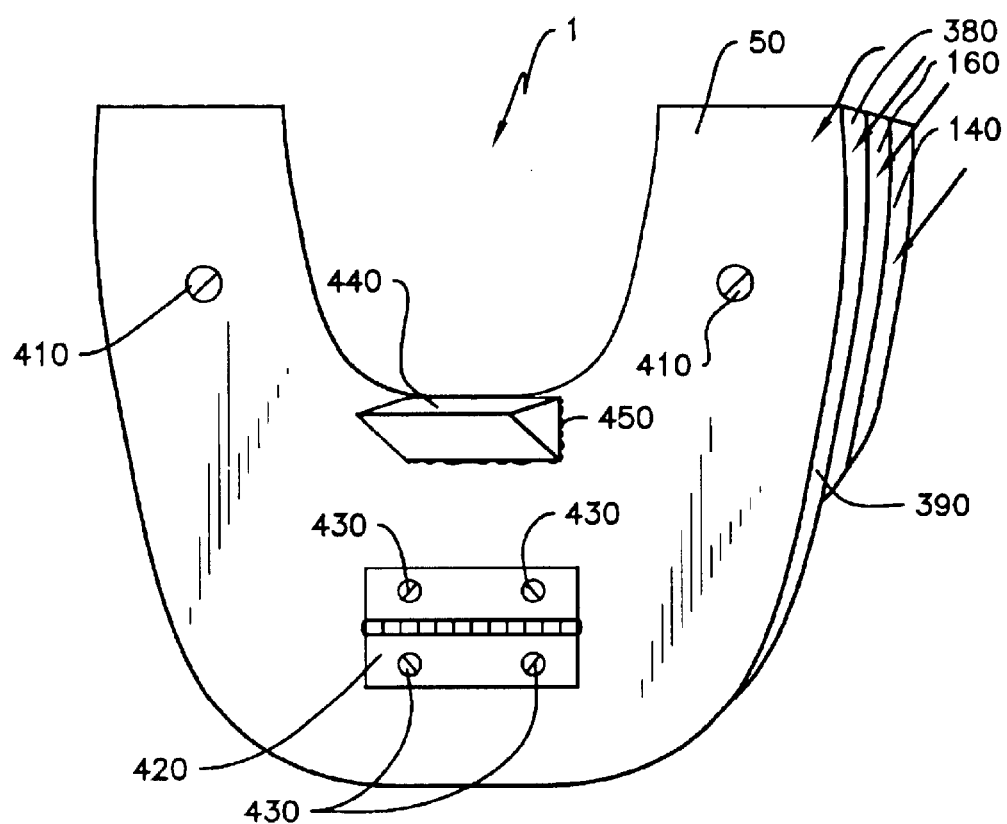
FIG. 9 is an exploded view of the brace (10) showing the interconnection plate and interconnection plate segment and the movement facilitation means.
Figure 10:
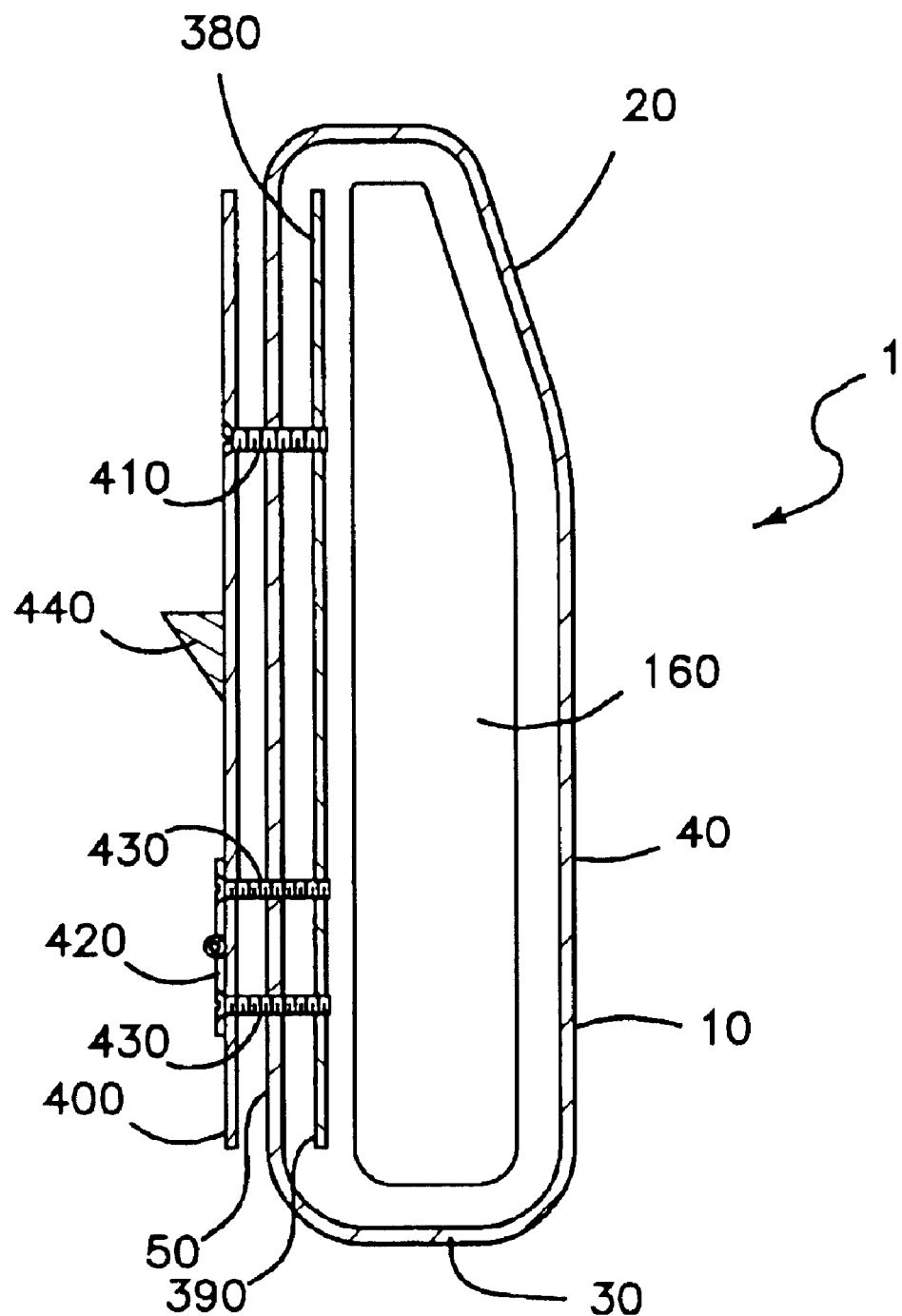
FIG. 10 is a section from FIG. 8 showing a body harness (370), the brace (10), the interconnection plate (380), interconnection plate segment (390), body harness attaching segment (400), body harness attaching means (410), movement facilitation means (420) and movement facilitation affixing means (430).

In an alternative embodiment the brace assembly (1) will be affixed to a body harness (370). Such is seen in FIGS. 8, 9 and 10. The body harness (370), in essence an "X" harness fitted around a patient's torso, provides a body support means between the patient and a brace (10). Body support affixing means comprised of body harness attaching means affixing the body harness (370) to the brace assembly (1). Such affixing, in an alternative embodiment, is expected to be an interconnection between the body harness (370) and one or more of the back side (50), first side (60) and or second side (70). As seen in FIG. 8, the brace assembly (1) for use in an alternative embodiment relative to a body harness (370), will have an interconnection plate (380) provided by interconnection structural means at the inside (140) or at the back side (50). The interconnection structural means is depicted in FIG. 9 as an interconnection plate (380), which may, in an embodiment, be segmented as depicted by the illustrated interconnection plate segment (390). The interconnection plate (380) and where used the interconnection plate segment (390), will be a rigid material generally composed of a metal, plastic, or other rigid material capable of receiving screw, rivet, bolt, adhesive, Velcro®, and other similar interconnection structural means (410) identified here as body harness attaching means (410)

and other such interconnection structural means (410) as will be appreciated as equivalent and as will be appreciated by those of ordinary skills in the art. Additionally, the brace assembly (1) may be so affixed to the body harness (370) at the brace first side (60) and or second side (70).

The body harness (370) has an attaching segment (400) comprising, in this alternative embodiment, a chest centrally located portion of the body harness (370) likely comprised of canvas or other such heavy weight cloth or plastic fabric as will be appreciated by those in the arts. As with the brace assembly (1), the material will be preferred to be an easily cleaned and moisture resistant material. As depicted in FIG. 10, the interconnection of the brace assembly (1) and the body harness attaching segment (400), may be composed of rivet, screw, bolt, sewing, adhesive, adhering means, Velcro®, and other attaching device means (410) between the body harness attaching segment (400) and one or more of the back side (50), first side (60), second side (70) and brace attaching segment (400). Additionally, for ease of movement of a patient in bending, a movement facilitation means (420) will allow flexion of the brace (10) intermediate the top edge (10) and the bottom edge (20). In FIG. 9 the movement facilitation means (420) is depicted as a hinge (420) fixed with movement facilitation affixing means (430) shown as screws, rivets and other such equivalent affixing means, from the back side (50) to the interconnection plate (380) and interconnection plate segment (390). It will be appreciated that the interconnection plate (380) may terminate at a point above the brace (10) bottom edge (30) such that no movement facilitation means (420) is required. Additionally, as seen in FIGS. 9, 10 and 11, for proper positioning of the brace (10) top edge (20) proximal the chin and away from the neck, a brace positioning means (440) will be provided generally intermediate the first side (60) and second side (70) which will displace the top edge (20) away from the patient thereby placing the top edge (20) proximal the patient's chin. The brace positioning means (440) will either proximal the top edge (20) and distal the bottom edge (30) or shaped to provide a spacer at which will act against the patent's body to urge the top edge (20) away from the body and neck and toward the chin. It will be appreciated that the brace positioning means (440) may be a block of foam proximal the top edge (20) or a block of foam or other semi rigid or rigid material with a generally triangular shape such that the width of the brace positioning means (440) is greater proximal the top edge (20) and narrower proximal the bottom edge (30). Such a brace positioning means (440) may be contained at the inside (140) within the brace (10) proximal the back side (50) or at the back side (50), secured with brace positioning affixing means (450) comprising adhesive or other equivalent affixing materials. With the brace positioning means (440) present it will be required to have the interconnection plate (380) and interconnection plate segment (390) positioned such there is an interconnection plate acute angle (460) between the interconnection plate (380) and the interconnection plate segment (390). The interconnection plate acute angle (460) may be accomplished by a bend in the plate such that the interconnection plate segment (390) formed creating such an interconnection plate acute angle (460) or the movement facilitation means (420) may be fixed and immobile once the acute angle is accomplished.

While a preferred embodiment of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

I claim:
1. A brace assembly comprising:
   a. a substantially planar brace (10) having a top-edge (20), a bottom edge, a front and a back side (50) and a first side (60) and a second side: (70);
   b. the top edge (20) forming an upfacing "c" shape (80); the brace (10) having a first width (w1) (90), from the front side (40) to the back-side (50) intermediate the top edge (20) and the bottom edge; the top edge (20) having a second width (w2) (100) from the front side (40) to the back side (50); the second width (w2) (100) less than the first width (w1) (90);
   c. body support attaching means affixed by affixing means to the brace (10); interconnection of the brace (10) and a body support means;
   d. the planar brace (10) having an outside (130) and an inside (140); opening and closing means at one or more of the top edge, bottom edge, first side (60), second side (70), front side (40) and back side (50): the opening and closing means when opened allowing insertion or retraction of an interior form (160); the opening and closing means when closed retaining the interior form (160);
   e. the width of the brace (10) increasing at the front side (40) from the top edge (20) toward the first width (w1) (90) intermediate the top edge (20) and the bottom edge (30) such that a sloped surface is formed at the front side (40) from the top edge (20) toward the first width (w1) (90) intermediate the top edge (20) and the bottom edge;
   f. the upfacing "c" shape (80) at the top edge (20) sized to receive and support a patient's chin; the top edge (20) constructed of a chin and head movement enabling means material (330);
   g. body support means comprised of one or more shoulder bars; body support affixing means comprised of a first shoulder bar attaching means (110) affixed by affixing means (180) and extending from the first side (60); a second shoulder bar attaching means (120) affixed by affixing means (180) and extending from the second side (70).

2. A brace of claim 1 further comprising:
   a. the top edge, bottom edge, first side (60), second side (70), front side (40) and back side (50) and first and second shoulder bar attaching means (120) constructed from a liquid resistant means material (340).

3. A brace of claim 2 further comprising:
   a the liquid resistant means material (340) comprised of a plastic material;
   b. the first shoulder bar attaching means (110) having an affixing surface (170); the second shoulder bar attaching means (120) having an affixing surface (170); the affixing surface (170) receiving affixing means (180); the first shoulder bar attaching means (110) and the second shoulder bar attaching means (120) comprised of a flexible planar material.

4. A brace of claim 3 further comprising:
   a. the interior form (160) comprised of a semi-rigid material means; the interior form (160) having a form top edge, a form bottom edge, a form front and a form back side, and a form first side (250) and a form second side (260);
   b. the form top edge (210) forming an upfacing "c" shape (80); the form having a third width (w3), from the form front side (230) to the form back side, intermediate the form top edge (210) and the form bottom edge; the form top edge (210) having a fourth width (w4) from the form front side (230) to the form back side; the third width (w3) less than the third width (w4).

5. A brace of claim 4 further comprising:
a. opening and closing means at one or more of the top edge, bottom edge, first side (60), second side (70), front side (40) and back side (50) comprised of an form receiving opening from the outside to the inside; the form receiving opening secured by opening and closing means including zipper, Velcro®; snaps or other opening and closing means;
b. the top edge, bottom edge, first side (60), second side (70), front side (40) and back side (50) and first and second shoulder bar attaching means (120) liquid resistant means material (340) and the top edge (20) movement enabling means material (330) comprised of a plastic, Naugahyde, leather or water proofed fabric;
c. the affixing means (180) at the affixing surface (170) comprised of zippers, Velcro®; snaps or other affixing means (180); the affixing means (180) formed to be received by shoulder bars on a wheelchair;
d. the interior form (160) semi-rigid material means composed of foam means; foam means comprised of foam rubber or polymer foam.

6. A brace of claim 1 further comprising:
a. the planar brace (10) having an outside (130) and an inside (14a); opening and closing means at one or more of the top edge, bottom edge, first side (60), second side (70), front side (40) and back side (50); the opening and closing means when opened allowing insertion or retraction of an interior form (160); the opening and closing means when closed retaining the interior form (160);
b. the width of the brace (10) increasing at the front side (40) from the top edge (20) toward the first width (w1) (90) intermediate the top edge (20) and the bottom edge (30) such that a sloped surface is formed at the front side (40) from the top edge (20) toward the first width (w1) (90) intermediate the top edge (20) and the bottom edge;
c. the upfacing "c" shape (80) at the top edge (20) sized to receive and support a patient's chin; the top edge (20) constructed of a chin and head movement enabling means material (330);
d. body support means comprised of a body harness affixed by a body harness affixing means to the body of a patient; body support affixing means comprised of a body harness attaching means affixed by the body harness affixing means at one or more of the back side (50), first side (60) and second side (70);
e. a brace positioning means (440) positioned intermediate the first side (60) and second side (70) proximal the back side (50) and proximal the top edge (20);
f. an interconnection plate acute angle (460) formed between the interconnection plate (380) and the interconnection plate segment (390).

7. A brace of claim 6 further comprising:
a. the top edge, bottom edge, first side (60), second side (70), front side (40) and back side (50) constructed from a liquid resistant means material (340);
b. the body harness (370) having an attaching segment (400); body harness attaching means (410), for interconnection of the brace assembly (1) and the body harness attaching segment (400), composed of rivet, screw, bolt, sewing, adhesive, adhering means, Velcro®, and other attaching devices between the body harness attaching segment (400) and one or more of the back side (50), first side (60), second side (70) and interconnection plate (380) and interconnection plate segment(390);
c. a movement facilitation means (420) affixed by movement facilitation affixing means (430) to the interconnection plate (380) and interconnection plate (390) allowing flexion of the brace (10) intermediate the top edge (10) and the bottom edge (20).

8. A brace of claim 7 further comprising:
a. the liquid resistant means material (340) comprised of a plastic material;
b. movement facilitation means (420) composed of a hinge (420); movement facilitation affixing means (430) composed of screw, rivet or equivalent affixing means; interconnection plate (380) and interconnection plate segment (390) composed of a rigid plate of metal or the equivalent.

9. A brace of claim 8 further comprising:
a. the interior form (160) comprised of a semi-rigid material means; the interior form (160) having a form top edge, a form bottom edge, a form front and a form back side, and a form first side (250) and a form second side (260);
b. the form top edge (210) forming an upfacing "c" shape (80); the form having a third width (w3) from the form front side (230) to the form back side, intermediate the form top edge (210) and the form bottom edge; the form top edge (210) having a fourth width (w4) from the form front side (230) to the form back side; the third width (w3) less than the fourth width (w4).

10. A brace of claim 9 further comprising:
a. opening and closing means at one or more of the top edge, bottom edge, first side (60), second side (70), front side (40) and back side (50) comprised of an form receiving opening from the outside to the inside; the form receiving opening secured by opening and closing means including zipper, Velcro®; snaps or other opening and closing means;
b. the top edge, bottom edge, first side (60), second side (70), front side (40) and back side (50) formed from liquid resistant means material (340) and the top edge (20) formed of movement enabling means material (330) comprised of a plastic, Naugahyde, leather or water proofed fabric;
c. the interior form (160) semi-rigid material means composed of foam means; foam means comprised of foam rubber or polymer foam.

* * * * *